United States Patent
Tandri et al.

(10) Patent No.: US 11,052,261 B2
(45) Date of Patent: *Jul. 6, 2021

(54) METHOD AND DEVICE FOR TREATING CARDIAC ARRHYTHMIAS

(71) Applicant: THE JOHNS HOPKINS UNIVERSITY, Baltimore, MD (US)

(72) Inventors: Harikrishna Tandri, Ellicott City, MD (US); Ronald David Berger, Baltimore, MD (US); Seth Weinberg, Williamsburg, VT (US); Leslie Tung, Baltimore, MD (US); Henry Halperin, Baltimore, MD (US); David Hunter, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 194 days.

This patent is subject to a terminal disclaimer.

(21) Appl. No.: 15/826,498

(22) Filed: Nov. 29, 2017

(65) Prior Publication Data
US 2018/0085594 A1    Mar. 29, 2018

Related U.S. Application Data

(63) Continuation of application No. 14/604,457, filed on Jan. 23, 2015, now Pat. No. 10,532,216, which is a
(Continued)

(51) Int. Cl.
*A61N 1/39* (2006.01)
*A61N 1/362* (2006.01)
(Continued)

(52) U.S. Cl.
CPC ............ *A61N 1/3962* (2013.01); *A61N 1/06* (2013.01); *A61N 1/3621* (2013.01);
(Continued)

(58) Field of Classification Search
CPC .. A61N 1/3956; A61N 1/3962; A61N 1/3624; A61N 1/06; A61N 1/3621;
(Continued)

(56) References Cited

U.S. PATENT DOCUMENTS

| 3,527,229 A | 9/1970 | Kempen |
| 5,184,616 A | 2/1993 | Weiss |

(Continued)

OTHER PUBLICATIONS

De Sanctis, Roman W.: "*Electrical Conversion of Ventricular Tachycardia*"; JAMA, Feb. 22, 1965, 191:8, pp. 96-100.
(Continued)

*Primary Examiner* — Tammie K Marlen
(74) *Attorney, Agent, or Firm* — DLA Piper LLP (US)

(57) ABSTRACT

The present invention provides both methods and devices for termination of arrhythmias, such as ventricular or atrial tachyarrhythmias. The device and method involves application of alternating current (AC) for clinically significant durations at selected therapeutic frequencies through the cardiac tissue to a subject experiencing arrhythmia. Methods are also provided to minimize or eliminate pain during defibrillation.

41 Claims, 9 Drawing Sheets

Related U.S. Application Data continuation of application No. 14/162,604, filed on Jan. 23, 2014, now abandoned, which is a continuation-in-part of application No. 13/393,821, filed as application No. PCT/US2010/047859 on Sep. 3, 2010, now abandoned.

(60) Provisional application No. 61/239,470, filed on Sep. 3, 2009.

(51) Int. Cl.
    *A61N 1/06*     (2006.01)
    *A61N 1/365*     (2006.01)

(52) U.S. Cl.
    CPC ......... *A61N 1/3624* (2013.01); *A61N 1/3625* (2013.01); *A61N 1/36514* (2013.01); *A61N 1/395* (2013.01); *A61N 1/3906* (2013.01); *A61N 1/3956* (2013.01); *A61N 1/3987* (2013.01)

(58) Field of Classification Search
    CPC .............. A61N 1/3625; A61N 1/36514; A61N 1/3906; A61N 1/395; A61N 1/3987
    See application file for complete search history.

(56) References Cited

U.S. PATENT DOCUMENTS

| | | |
|---|---|---|
| 5,609,618 A | 3/1997 | Archer |
| 5,632,267 A | 5/1997 | Hognelid et al. |
| 5,792,189 A | 8/1998 | Gray et al. |
| 6,091,989 A | 7/2000 | Swerdlow et al. |
| 6,120,499 A | 9/2000 | Dickens et al. |
| 6,317,631 B1 | 11/2001 | Ben-Haim et al. |
| 6,408,205 B1 | 6/2002 | Renirie et al. |
| 6,633,778 B2 | 10/2003 | Sherman |
| 6,991,002 B2 | 1/2006 | Osborne |
| 7,174,208 B2 | 2/2007 | DeGroot |
| 7,522,958 B2 | 4/2009 | Ideker |
| 7,555,338 B2 | 6/2009 | Ostroff |
| 7,643,876 B2 | 1/2010 | Zhang |
| 7,684,870 B1 | 3/2010 | Kroll |
| 8,036,754 B2 | 10/2011 | Lee |
| 8,214,033 B2 | 7/2012 | Snell |
| 2006/0259195 A1 | 11/2006 | Eliuk |
| 2008/0058877 A1* | 3/2008 | Zhang ................. A61N 1/3601 607/5 |
| 2008/0169043 A1 | 7/2008 | Osborne |
| 2010/0114207 A1 | 5/2010 | Snell et al. |
| 2010/0241190 A1 | 9/2010 | Kilgore et al. |
| 2010/0241270 A1 | 9/2010 | Eliuk |
| 2012/0215269 A1 | 8/2012 | Tandri et al. |

OTHER PUBLICATIONS

International Search Report dated Jun. 26, 2015 regarding PCT/US2015/012743.

\* cited by examiner

METHOD AND DEVICE FOR TREATING CARDIAC ARRHYTHMIAS

CROSS REFERENCE TO RELATED APPLICATION(S)

This application is a continuation of U.S. patent application Ser. No. 14/604,457, filed Jan. 23, 2015, now issued as U.S. Pat. No. 10,532,216; which is continuation-in-part of U.S. application Ser. No. 14/162,604, filed Jan. 23, 2014, now abandoned; which is a continuation-in-part application of U.S. application Ser. No. 13/393,821, filed Apr. 30, 2012, now abandoned; which is a 35 U.S.C. § 371 National Stage application of International Application No. PCT/US2010/047859 filed Sep. 3, 2010, which claims the benefit under 35 U.S.C. § 119(e) to U.S. Ser. No. 61/239,470 filed Sep. 3, 2009. The disclosure of each of the prior applications is considered part of and is incorporated by reference in the disclosure of this application.

BACKGROUND OF THE INVENTION

Field of the Invention

The present disclosure relates generally to medical treatments and more specifically to a method and device for treating arrhythmias of the heart, such as tachycardia and cardiac fibrillation.

Background Information

Arrhythmia is a variation from the normal rhythm of the heart beat. Cardiac arrhythmias are an important cause of morbidity and mortality. The major cause of fatalities due to cardiac arrhythmias is the subtype of ventricular arrhythmias known as ventricular fibrillation (VF). Conduction of electrical impulse is a unique property of cardiac and skeletal muscle and nervous tissue and is fundamental to their physiologic function. Abnormal cardiac electrical impulse generation and propagation underlies the pathogenesis of several diseases, including ventricular fibrillation (see, Santinelli et al., *Int J Cardiol.*, 3(1):109-111 (1983); Kanani et al., *J Cardiovasc Pharmacol.* 32(1):42-48 (1998); and Amitzur et al., *Cardiovasc Drugs Ther.*, 17(3):237-247 (2003)), a leading cause of death in the developed world.

To stop VF in an attempt to return the heart to a normal rhythm, automatic external defibrillators (AED) are widely in use in healthcare and non-healthcare settings. In addition, implantable defibrillators are highly useful in management of a number of chronic heart conditions. For example, Sudden Cardiac Death (SCD), which is often due to ventricular fibrillation, accounts for over 400,000 deaths annually in the United States. Several clinical trials have shown survival benefit in SCD survivors who receive implantable defibrillators. Recent trials have also shown that patients who are at risk for SCD also benefit from this therapy and implantable defibrillators have been used in this population with significant reduction in mortality.

The physical structure of defibrillator systems can be generally illustrated with reference to the implantable format. Such defibrillator systems contain a hermetically sealed "Can" that houses the battery, electronic circuitry and capacitors. These devices are implanted in the chest wall and electrodes are deployed intravascularly to stimulate, pace and deliver high energy defibrillatory shocks to defibrillate the heart. The electrode/lead is typically placed through the subclavian vein into the endocardium.

Three modes of therapies are used by the implantable defibrillators to treat dangerous arrythmias: 1) anti-tachycardia pacing; 2) low energy cardioversion; and 3) high energy defibrillation. Among the three, only high energy defibrillaton has been shown to be effective in defibrillating the heart during ventricular fibrillation.

Several different electrode configurations have been used to deliver the high energy including, epicardial lead systems (U.S. Pat. Nos. 5,342,407 and 5,603,732), endocardial lead systems, and subcutaneous electrodes (U.S. Pat. Nos. 5,133, 353, 5,261,400, and 5,620,477). The housing of the defibrillator can also serve as an additional electrode during delivery of defibrillatory shocks and for pacing (U.S. Pat. No. 5,658,321). Recently, a totally subcutaneous-non-vascular system that is capable of delivering pacing and high voltage defibrillatory shocks has also been described (U.S. Pat. No. 7,536,222).

Currently the principal approach to terminating fibrillation using implantable or external systems is by delivering a high voltage DC shock to cause defibrillation of the heart. This is achieved by charging a capacitor and delivering the charge to the heart over a period of typically 4-16 msec. As such, the current defibrillator circuitry includes high performance capacitors capable of rapidly charging and discharging charge, causing a brief period of high current density in the myocardium that causes defibrillation. There may be multiple capacitors controlled by a circuit and typically 5-40 Joules of energy are delivered to achieve defibrillation.

While effective in many cases, existing defibrillation systems have drawbacks. For example, the energy delivered may be insufficient in magnitude or timing of delivery to stop fibrillation. Low frequency DC and AC are known to be pro-fibrilliatory. In addition, the large electric field applied in defibrillation also leads to significant skeletal muscle stimulation which has been implicated in the pain that follows defibrillation shocks.

Further, the current methodology used to treat cardiac arrhythmias using DC fields is associated with a host of adverse effects that include cellular injury by way of electroporation (see, Tung, *Methods Mol Biol.*, 48:253-271 (1995); Tung et al., *Ann N Y Acad Sci.*, 720:160-175 (1994); and Al-Khadra et al., *Circ Res.*, 87(9):797-804 (2000)), cardiac conduction disturbances (see, Kanani et al., *J Cardiovasc Pharmacol.*, 32(1):42-48 (1998); and Eysmann et al. *Circulation.*, 73(1):73-81 (1986)), mechanical dysfunction (see, Tung et al., *Ann N Y Acad Sci.*, 720:160-175 (1994); Mollerus et al., *J Intery Card Electrophysiol.*, 19(3):213-216 (2007); and Tokano et al., *J Cardiovasc Electrophysiol.*, 9(8):791-797 (1998)), and increased mortality due to heart failure (see, Moss et al., *N Engl J Med,* 346(12):877-883 (2002); and Bardy et al., *N Engl J Med,* 352(3):225-237 (2005)).

The present invention is based on the discovery of the previously unrecognized biophysical phenomenon of reversible cardiac conduction block using sustained AC fields that is without residual electrophysiological consequence and can be applied with less perceived pain than existing defibrillatory methods. Cardiac cells remain in a refractory state for the duration of field stimulation by elevation of $V_m$, a phenomenon that is distinctly different from the effect of DC fields. Further, the cell response to sustained AC fields appears to be devoid of the deleterious effects commonly observed during DC field stimulation. Hence, cardiac conduction block using AC may provide a safer alternative for terminating cardiac arrhythmias.

Low frequency AC (50-60 Hz) waveforms were the first form of electrical therapy used to treat VF, but was abandoned because of its high risk of proarrhythmia (see, Gurvich et al., *Am Rev Soy Med.*, 4(3):252-256 (1947); Smith et al., *Am J PathoL*, 47:1-17 (1965); and Lown et al. *Am J Cardiol*, 10:223-233 (1962). Indeed, 50 Hz AC has successfully found its way into the current generation implantable defibrillators as an efficient way to induce VF (see, Malkin et al., *Med Biol Eng Comput.*, 41(6):640-645 (2003); and Mower et al. *Circulation.*, 67(1):69-72 (1983)).

However, few studies have evaluated the effects of higher AC frequencies in intact hearts. Previous studies used AC in intact guinea pig hearts and demonstrated a frequency-dependent increase in pacing threshold (see, Weirich et al. *Basic Res Cardiol.*, 78(6):604-616 (1983)) and fibrillation threshold (see, Weirich et al. *Basic Res Cardiol.*, 78(6):604-616 (1983); and Geddes et al., *Med Biol Eng.*, 7(3):289-296 (1969)) for frequencies up to the kilohertz range.

Roberts et al. evaluated the defibrillation efficacy of AC frequencies up to 1 kHz, but with a maximum duration of 32 cycles (Pacing Clin Electrophysiol., 26(2 Pt 1):599-604 (2003). They concluded that a 200 Hz, 2 cycle waveform was most effective to achieve external defibrillation.

Sweeney et al. used monophasic rectangular pulses for open chest defibrillation in dogs and showed that the energy and current requirement was significantly higher at frequencies >1 kHz (*J Cardiovasc Electrophysiol.*, 7(2):134-143 (1996).

All the above studies relied on defibrillation by the onset of the electric field, and none of the studies explored longer duration field pulses to block conduction as a way to prevent re-initiation of VF. Although conduction block might be expected in the range of frequencies tested in these previous studies, this biophysical phenomenon was not specifically explored. More importantly, the short duration of the high frequency AC field (2-32 cycles) might not have been sufficient to extinguish multiple reentrant wave fronts present in VF.

However, the cellular electrophysiological effects of sinusoidal AC field stimulation have not been systematically studied in cardiac tissue. Meunier et al. demonstrated prolongation of action potential duration in cardiac tissue subject to low frequency (50 Hz) sinusoidal AC stimulation (*J Cardiovasc Electrophysiol.*, 12(10):1176-1184 (2001); and *J Cardiovasc Electrophysiol.*, 10(12):1619-1630 (1999)). The plateau of the action potential remained elevated, and the amplitude of $V_m$ oscillation was inversely related to the frequency of AC field up to 100 Hz, the maximum frequency used in their study.

Frequency dependent conduction block in excitable tissue such as the neural axons and peripheral nerves have been demonstrated (see, Tanner, *Nature*, 195:712-713 (1962); and Woo et al., *Bulletin Los Angeles Neurological Society*, 29:87-94 (1964)). Kilgore et al. reported high frequency nerve conduction block in the peripheral nerve using 3-5 kHz biphasic current (Kilgore et al., *Med. Biol. Eng. Comput.*, 42:394-406 (2004)). Animal experiments have also shown that high-frequency alternating electrical current applied to peripheral nerves can block conduction of action potentials (see, Tanner, *Nature*, 195:712-713 (1962); Reboul et al., *Am. J. Physiol.*, 125:205-215 (1939); Rosenblueth et al., *Am. J. Physiol.*, 125:251-264 (1939); and Bowman et al., *Appl. Neurophysiol.*, 49:121-138 (1986)). This nerve block was quickly reversible once the stimulation was removed suggesting that this was not due to repeated stimulation resulting in fatigue (see, Kilgore et al., *Med. Biol. Eng. Comput.*, 42:394-406 (2004)). Subsequently, others have reported similar findings in a lumped circuit model of the myelinated axon based on Frankenhaeuser-Huxley model.

The mode of conduction block was demonstrated to be due to constant activation of potassium channels, thus antagonizing sodium channel induced depolarization (see, Zhang et al., *IEEE Trans. Biomed. Eng.*, 53:2445-54 (2006)). To date, however, such methods are not being applied to the heart; e.g., to minimize pain associated with the delivery of a defibrillating current.

Further, use of radio frequency (RF) energy has been used to produce temporary conduction block in local areas of a heart. U.S. Pat. No. 6,431,173 describes a method of using electrical energy to produce temporary conduction block in a local region of the patient's myocardium to disrupt a reentry pathway through which an atrial or ventricular tachycardia (or other type of arrhythmia) is initiated and perpetuated, thereby resulting in cardioversion or defibrillation. However, use of RF to for terminating tachyarrhythmias may cause permanent myocardial damage.

Based on the current state of treatment of arrhythmias, there is a need for an improved device and method to terminate cardiac fibrillation to provide less painful treatment of arrhythmias.

SUMMARY OF THE INVENTION

The present invention provides both a method and device for termination of arrhythmias, such as ventricular or atrial tachyarrhythmias. The device and method involves application of alternating current (AC) for clinically significant duration within a selected range of therapeutic frequencies applied through the cardiac tissue of a subject experiencing arrhythmia.

In one aspect, a method of treating cardiac arrhythmia in a subject in need thereof is provided. The method comprises administering a high frequency AC to a cardiac tissue of the subject, thereby treating the cardiac arrhythmia. In various embodiments, the AC is administered at a frequency between about 50 Hz to 20 KHz. In various embodiments, the AC is administered for a duration between about 0.025 to 2 seconds. In exemplary embodiments, the AC is administered for at least 0.050 or 0.100 seconds.

In another aspect of the invention, the method includes a tiered therapy to alleviate or treat cardiac arrhythmia. The method may include administration of AC in a staged progression of multiple tiers. For example, tiered therapy may include applying AC along a progression of different frequencies and durations, the progression continuing until the arrhythmia is terminated. As such, the method may include applying a series of different frequencies of AC, or AC in combination with DC, until the arrhythmia is terminated.

In another aspect of the invention, the method includes a combined approach to therapy to alleviate or treat cardiac arrhythmia as well as reducing pain. The method may include applying AC at different distinct frequencies to achieve neuromuscular blocking effects in addition to arrhythmia termination. In one embodiment, a first frequency of between about 1 kHz to 20 kHz is applied to achieve neuromuscular blocking effects, such a reduction in pain stimulus. In a related embodiment, a second frequency of between about 100 Hz to 1 kHz is applied to achieve arrhythmia termination. The frequencies may be applied simultaneously or the first frequency may be applied before the second to effectively block any pain associated with delivery of the second frequency.

In another aspect of the invention, the method includes a combined approach to therapy to alleviate or treat cardiac arrhythmia as well as reducing pain. The method may include applying AC at one or more frequencies in combination with an electric shock, such as a monophasic or biphasic shock. In one embodiment, application of the AC begins before application of the electric shock. In another embodiment, the electric shock is applied before application of the AC begins. In yet another embodiment, the electrical shock is monophasic, and the shock includes an onset prior to onset of the AC and the shock terminates after onset of the AC.

In various aspects and embodiments, the method includes detecting the occuyence of arrhythmia before, after or during the AC is administered.

In another aspect of the invention, a method for treating tacharrhythmia in a subject is provided for emergency life support of a subject having cardiac tissue that is in an intractably fibrillated state. The method includes administering a plurality of high frequency alternating current (AC) pulses to a cardiac tissue of the subject, wherein the cardiac tissue is in an intractably fibrillated state between administration of each AC pulse, thereby treating the tacharrhythmia. In one embodiment, each AC pulse has a duration of about 0.1 to 2 seconds. Pulsed AC application in this instance allows the cardiac muscle to fibrillate between AC pulses to achieve electrical activation of the ventricles and generation of a mechanical systole.

In another aspect, a device for treating arrhythmia is provided. The device includes a computer-readable program containing one or more algorithms for generating and/or delivering AC and/or electrical shock, a plurality of electrodes, a waveform generator generating high frequency AC and/or electrical shock, and optionally, a sensing circuit allowing detection of arrhythmia in a subject and automatic administration of AC. In one embodiment, the device is configured to generate AC having a frequency between about 50 Hz to 20 kHz in response to operation of the computer-readable program.

In another aspect of the invention, the device is configured to deliver tiered therapy to a subject to alleviate or treat cardiac arrhythmia. As such, in one embodiment, the device is configured to generate and apply one or more different frequencies of AC.

In another aspect of the invention, the device is configured to administer emergency assistance to a subject experiencing intractable cardiac fibrillation.

In various aspects and embodiments, the device of the present invention may be configured such that the plurality of electrodes are disposed intravascularly or intracardiacly, extravascularly or externally, or both. The device may be fully or partially implantable, or be configured wholly external to the subject.

In another aspect, a method of generating local conduction block of cardiac tissue is provided. The method includes administering alternating current (AC) to a targeted site of a heart during an arrhythmia to cause termination of the arrhythmia. In one embodiment, the AC is administered at a frequency between about 100 Hz to 1 kHz. In a related embodiment, the AC is delivered via a catheter including a plurality of electrodes. In various embodiments, delivery of the AC is timed to a surface electrocardiogram or an intracardiac electrocardiogram.

BRIEF DESCRIPTION OF THE DRAWINGS

FIG. 3A is a graphical representation of the effects of application of a 1 kHz AC field. FIG. 3B is a graphical representation of the effects of application of a 100 kHz AC field. FIG. 3C is a graphical representation of the effects of application of a 10 kHz AC field. In FIGS. 3A-3C, the top panels of each show voltage maps before, during, and after AC field. For each, the monolayer was paced from the left edge by a bipolar point electrode at 6 Hz (for A) or 3 Hz (for B and C). In FIGS. 3A-3C, the bottom panels in each case show a representative voltage trace from the center of the monolayer at site x. Vertical lines along the x-axis denote the time of point stimuli, while the gray bar denotes the time AC field is on. As shown, AC field stimulation is effective in producing propagation block when applied at some frequencies (e.g. 1000 Hz in FIG. 3A), but not at others (e.g. 100 Hz in FIG. 3B or 10 kHz in FIG. 3C).

FIG. 4A shows a series of voltage maps before, during, and after a 1 kHz 1-sec duration AC pulse. Numbers above maps denote time in msec. Maps with gray background indicate that the AC pulse is on. FIG. 4B shows a representative voltage trace from site a of FIG. 4A (top left) showing stable train of action potentials before the AC pulse, and sustained partial depolarization during AC delivery, with prompt return to resting potential when AC stimulation is turned off. Figure C shows voltage traces at sites a-f of FIG. 4A (top row) at an expanded time scale at the time of AC field onset. In FIGS. 4B and 4C, the gray bar denotes the time the AC pulse was on.

FIG. 6A shows a plot summarizing conduction experiments. In conduction experiments, the response during the pulse was characterized as no effect, field-evoked activity (FEA), or block, as described in FIG. 3. Post-pulse ectopic activity (PPEA), as shown in FIG. 3, was also identified separately. FIG. 5B shows a plot summarizing reentry experiments. In reentry experiments, the response was characterized as no effect, FEA+termination, termination, or re-initiation, as described in Examples. Note similarity in the parameter spaces for conduction and reentry, with regions of block in FIG. 5A corresponding to termination in FIG. 5B (X for each), FEA in FIGS. 5A and 5B (triangles), and no effect (circles).

FIGS. 6A and 6B show graphical representations of simulations of AC field pulses. In both FIGS. 6A and 6B, the top panels show voltage maps before, during, and after a 500 Hz, 300-arbitrary units (a.u.) field strength, 1-sec duration AC pulse. Time (in msec) is denoted above the maps. Maps with gray background denote times during which the AC pulse is on. In both FIGS. 6A and 6B, the bottom panels show the transmembrane voltage ($V_m$), sodium current ($I_{Na}$), and intracellular calcium ($[Ca]_i$) at a site denoted by the pink dot on the first voltage map. The gray bar denotes the time the AC field pulse is on. FIG. 6A shows application of 500

Hz AC field. Vertical lines along the lower x-axis denote the times of point stimuli. FIG. 6B shows application of a 500 Hz AC field.

FIG. 9A shows an illustrative ascending high frequency AC ramp followed immediately by biphasic shock. FIG. 9B shows skeletal muscle force response (black) to ramped high frequency AC stimulation that precedes 400 V biphasic shock (grey). FIG. 9C shows muscle force response (black) to 400 V biphasic shock alone (grey).

DETAILED DESCRIPTION OF THE INVENTION

Figure 1:
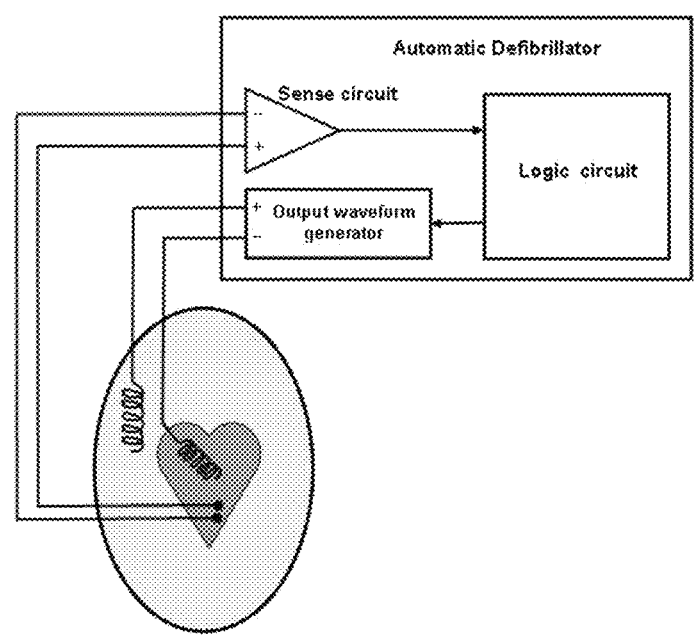
FIG. 1 shows a graphical representation of one embodiment of the device of the present invention, wherein the device is configured as an automatic internal defibrillator (AID).
Figure 2:
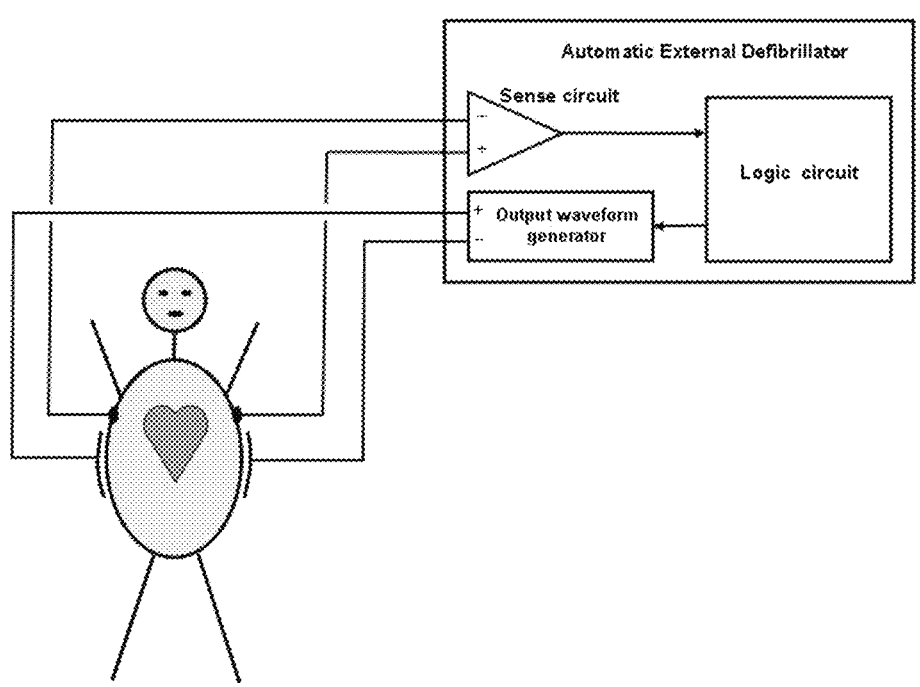
FIG. 2 shows a graphical representation of one embodiment of the device of the present invention wherein the device is configured as an automatic external defibrillator (AED).
Figure 3:
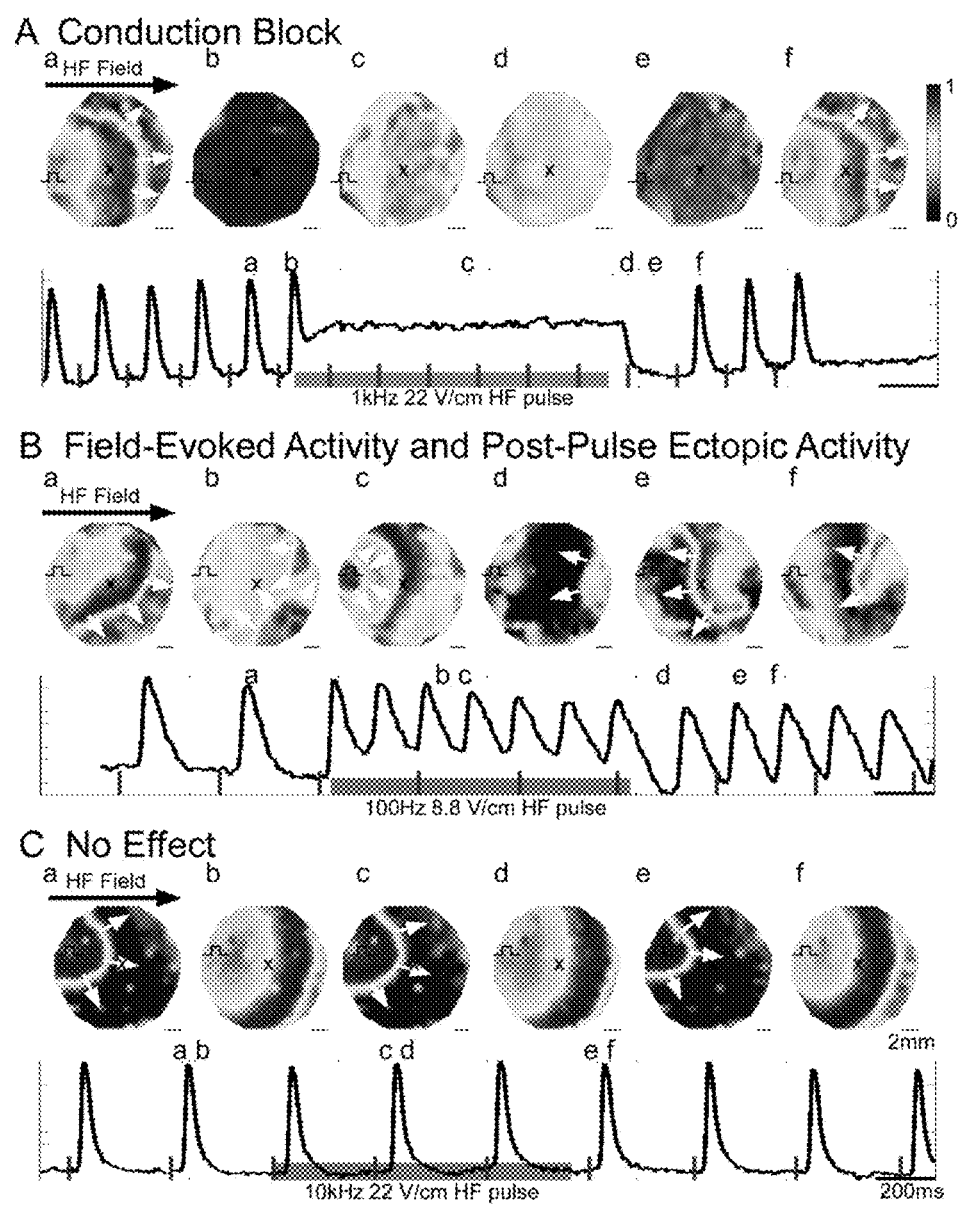
FIGS. 3A, 3B and 3C show graphical representations of the effects of AC electric field stimulation on propagation of paced impulses across confluent monolayers (n=15) of neonatal rat ventricular cardiomyocytes.

The present invention provides methods for using selected therapeutic frequencies of AC to cause termination of arrhythmia. The mechanisms by which the AC terminates arrhythmia are based on the generation of positively- and negatively-polarized areas in the heart by the applied field, separately by a voltage gradient. The sequential reversal of the polarity of these regions of membrane polarization by the applied AC, combined with the non-linear response of the membrane to the shock-induced polarization, results in a sequential decrease in the voltage gradient between the regions of opposite polarity until this gradient reaches a value that is insufficient for the generation of a new wavefront at the border between regions of opposite membrane polarity. The frequency range minimizes proarrythmia, which has been the major drawback of low frequency electrical current. The invention provides additional embodiments wherein the high frequency AC is provided in combination with AC at other frequencies or DC in a tiered therapy to terminate arrhythmia and/or co-terminously to block pain.

Thus, the present invention provides an alternative mechanism to use of DC fields to achieve termination of cardiac arrhythmias by causing conduction block using sustained AC field. It is expected that AC field-induced, reversible conduction block will have widespread applicability in both external and implantable medical devices to treat arrhythmias. Finally, based the observations discussed herein using AC in cardiac tissue, in conjunction with reports on nerve block using high frequency AC, it can be expected that AC stimulation could be utilized to block both cardiac and nerve conduction during arrhythmias to achieve painless defibrillation.

Before the present devices and methods are described, it is to be understood that this invention is not limited to particular devices, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is based in part on the discovery of a novel biophysical phenomenon of reversible block of cardiac conduction during sustained sinusoidal alternating current (AC) field stimulation. While not wishing to be bound by any theory as to mechanism of action, it is believed that, when applied according to the invention, an appropriate (not pro-fibrillatory) AC field paralyzes affected cardiac cells by maintaining them in a partially depolarized state and rendering them refractory to pacing stimuli. This effect is completely reversible on cessation of the AC field (see, e.g., Example 1 and FIGS. 3-7). AC field terminated reentrant spiral waves by depolarizing the entire excitable gap and maintaining an elevated transmembrane potential ($V_m$) throughout the monolayer, thus preventing re-initiation of reentry. Computer simulations of sustained AC field in a three-dimensional bidomain model of guinea pig ventricular myocardium reproduced the conduction block and revealed inactivation of Na channels for the duration of the field. Cardiac conduction was unaffected during direct current field, suggesting that conduction block was unique to sustained AC stimulation.

As such, the present invention is based on the seminal discovery of a reversible conduction block in cardiac tissue using sustained AC field that provides a novel method to terminate cardiac arrhythmias. Reversible conduction block by AC has broad applicability in clinical cardiac electrophysiology.

The present invention provides both a method and device for termination of arrhythmias, such as ventricular or atrial tachyarrhythmias. The device and method involves application of high frequency alternating current or electric field through the cardiac tissue to a subject experiencing arrhythmia, such as tachyarrhythmia.

In one aspect, a method of treating cardiac arrhythmia in a subject in need thereof is provided. The method comprises administering a high frequency alternating current (AC) to a cardiac tissue of the subject, thereby treating the cardiac arrhythmia.

In another aspect of the invention, the method includes a combined approach to therapy to alleviate or treat cardiac arrhythmia as well as reducing pain. The method may include applying AC at different distinct frequencies to achieve neuromuscular effects in addition to arrhythmia termination. In one embodiment, a first frequency of between about 1 kHz to 20 kHz is applied to achieve neuromuscular effects, such a reduction in pain stimulus. In a related embodiment, a second frequency of between about 100 Hz to 1 kHz is applied to achieve arrhythmia termination. The frequencies may be applied simultaneously or the first frequency may be applied before the second to effectively block any pain associated with delivery of the second frequency.

In another aspect of the invention, the method includes a combined approach to therapy to alleviate or treat cardiac arrhythmia as well as reducing pain. The method may include applying AC at one or more frequencies in combination with an electric shock, such as a monophasic or biphasic shock. In one embodiment, application of the AC begins before application of the electric shock. In another embodiment, the electric shock is applied before application of the AC begins. In yet another embodiment, the electrical shock is monophasic, and the shock includes an onset prior to onset of the AC and the shock terminates after onset of the AC.

In various aspects and embodiments, the method includes detecting the occurrence of arrhythmia before, after or during the AC is administered.

In another aspect of the invention, a method for treating tacharrhythmia in a subject is provided for emergency life support of a subject having cardiac tissue that is in an intractably fibrillated state. The method includes administering a plurality of high frequency alternating current (AC) pulses to a cardiac tissue of the subject, wherein the cardiac tissue is in an intractably fibrillated state between administration of each AC pulse, thereby treating the tacharrhythmia. In one embodiment, each AC pulse has a duration of about 0.1 to 2 seconds. Pulsed AC application in this instance allows the cardiac muscle to fibrillate between AC pulses to achieve electrical activation of the ventricles and generation of a mechanical systole.

In another aspect, a method of generating local conduction block of cardiac tissue is provided. The method includes administering alternating current (AC) to a targeted site of a heart during an arrhythmia to cause termination of the arrhythmia. In one embodiment, the AC is administered at a frequency between about 100 Hz to 1 kHz. In various embodiments, delivery of the AC is timed to a surface electrocardiogram or an intracardiac electrocardiogram. In one embodiment the method of local conduction block is used during diagnostic or therapeutic electrophysiologic procedures, where the arrhythmia is electrically mapped and a region critical to the arrhythmia is identified using a catheter based approach. To decide whether to ablate the region, before application of therapeutic energy (RF or Cryo), alternating current is applied locally to cause conduction block. If this terminates the arrhythmia then this information will be useful both for diagnostic and therapeutic purposes.

Ablation may be performed as described in U.S. Pat. No. 6,431,173. There are two types of ablative therapy, namely, surgical and catheter ablative therapy. The aim of either type of ablative therapy is to permanently destroy (irreversibly damage) the myocardium which constitutes the critical part of the reentrant circuit of the ventricular or a trial tachycardia which is required to sustain or perpetuate the ventricular or a trial tachycardia. In other words, the ablation of the critical region of the myocardium acts to permanently eliminate the conduction or impulse formation through the reentrant pathway which is required to sustain or perpetuate the ventricular or a trial tachycardia. Successful ablation is critically dependent on the ability to localize the involved myocardium necessary to initiate and perpetuate the ventricular or a trial tachycardia. Diagnostic techniques used to localize the reentry circuit include analysis of a 12-lead ECG, catheter mapping during a trial or ventricular tachycardia, and pace mapping. Once the site of origin of ventricular or a trial tachycardia is localized, ablative procedures (surgical or catheter directed) can be performed.

In the catheter ablation approach, catheter-based electrodes are used to permanently disable myocardium tissue adjacent to the electrode without affecting more distant tissue.

Using RF energy (500-1000 kHz, 15-50 W, 100-800 J, 30-75 V rms and 0.1-1 A rms, for 10-60 sec.), tissue extending several mm from the electrode is heated to 65-100° C. This produces permanent lesions that block reentry or disable the AV node. Particularly in the case of atrial fibrillation, specific anatomical structures are often associated with reentry pathways required to sustain arrhythmias. As a result, the incidence of arrhythmias may decrease and/or the arrhythmias may be better organized, thereby leading to a higher degree of success with low energy shock therapies. One example of a critical isthmus of conduction for atrial flutter cited by Lesh and co-workers, is found in the lower right atrium extending from the inferior vena cava to the coronary sinus ostium bordered by the eustachian ridge (ER) and the tricuspid annulus (TA). Lesh et al. also speculate that any lesion connecting the ER/crista terminals and the TA could interrupt the atrial flutter reentrant circuit. Although the reentrant pathways for AF are more complex and possibly shorter and more numerous, some success has been achieved with the use of multiple lesions to cure AF.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the term "administration" or "administering" are intended to include an act of applying or delivering alternating current to cardiac tissue or cells. Typically administration is performed via externally disposed or implanted electrodes as described herein.

In another aspect, a device for treating arrhythmia is provided. The device includes a computer or microprocessor-readable program containing one or more algorithms for generating and/or delivering AC and/or electrical shock, a plurality of electrodes, a waveform generator generating high frequency AC and/or electrical shock, and optionally, a sensing circuit allowing detection of arrhythmia in a subject and automatic administration of AC.

As used herein, high frequency (HF) alternating current (AC) is intended to include frequencies of between about 50 Hz and 20 kHz. In various aspects and embodiments, for termination of arrhythmia and pain management, the device and method utilize frequencies of between about 50 Hz and 1 kHz, 50 Hz and 900 Hz, 50 Hz and 800 Hz, 50 Hz and 700 Hz, 50 Hz and 600 Hz, 50 Hz and 500 Hz, 100 Hz and 500 Hz, 100 Hz and 400 Hz, 100 Hz and 300 Hz, 100 Hz and 200 Hz, 150 Hz and 500 Hz, 150 Hz and 400 Hz, 150 Hz and 300 Hz, 150 Hz and 200 Hz, 500 Hz to 1 kHz and 250 Hz to 500 Hz. Frequencies above 1 kHz are anticipated to be ineffective. Further, it is anticipated that most effective results will be obtained, depending to a degree on duration, within frequency ranges of 150 Hz and 300 Hz, including at 200 Hz.

As will be appreciated by those in the art, in various aspects and embodiments of the invention, alternating current may be delivered in any number of waveforms or combinations or waveforms. In various embodiments, the waveform may be a sinusoidal, triangular, or square-wave, as well as any combinations thereof. Additionally, square-waves, may have a duty-cycle of about 25%, 30%, 35%, 40%, 45%, 50%, 55%, 60%, 65%, 70%, or 75%. Further, the waveform may switch on or off abruptly, or may be shaped by an envelope waveform to effect more gradual onset or offset.

In practicing the invention, alternating current may be applied or administered for various durations of time ranging from about 0.025 second to 2 seconds to accomplish termination of the arrhythmia. In various embodiments, alternating current may be applied or administered for about 0.025 second to 1.5 seconds, or 0.025 second to 1 second, 0.025 to 0.5 second. For example, alternating current may be applied or administered for about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 seconds.

As will also be appreciated by those in the art, in various aspects and embodiments of the invention, alternating current may be delivered in a ramped waveform, e.g., a waveform having increasing amplitude over time. Such waveforms are useful for blocking or decreasing sensitivity of the muscle to a subsequent delivery of an electrical shock, e.g., a monophasic shock, a biphasic shock, or a combination thereof. High frequency AC administered via a ramped waveform blunts the amplitude and the rate of force developed in skeletal muscle, which results in substantial mitigation of defibrillation-induced pain.

A ramped waveform of the present invention employs an extended, gradual rise, instead of rising rapidly to its maximum level. The rise time of the ramped waveform should be a substantial portion of the duration of the waveform and, preferably, at least about 50%, 60%, 70%, 80%, 90%, 95% or greater, of the total duration of the waveform. The ramped waveform may be applied or administered for various durations of time ranging from about 0.025 second to 2 seconds to accomplish termination of the arrhythmia. In some embodiments, ramped alternating current may be applied or administered for about 0.025 second to 1.5 seconds, or 0.025 second to 1 second, 0.025 to 0.5 second. For example, ramped alternating current may be applied or administered for about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.0 seconds or greater. Generally, the maximum reduction in muscle stimulation occurs with a fully ramped waveform, for example, 1 second total duration and approximately a 1 second rise time. After reaching the maximum current level, the output pulse may continue at this current level for a short period of time, and then rapidly returns to 0 over a short fall time. The time period during which the pulse is at its maximum current level may be, for example, 0-0.1 seconds. As such, the ramped waveform may begin with an increased amplitude that continues to increase, level off, or otherwise change.

In various embodiments, a high frequency waveform may be continuously ramped in amplitude during the total duration of application. The amplitude may be ramped from about 0 to 25, 50, 75, 100, 125, 150, 175, 200, 225, 250, 300, 350, 400 or 500 volts or greater.

In various embodiments, the present invention contemplates administration of a ramped waveform in combination with an electrical, for instance, a monophasic or biphasic shock. The electrical shock may follow the ramped waveform. In one embodiment, the shock waveform that is administered to the high frequency AC ramp is a decaying exponential with time constant 1-10 ms. The peak rising edge voltage of the shock may be less than, equal to, or greater than the peak of the high frequency AC ramp. In embodiments, the peak rising edge voltage of the shock is greater than the peak of the high frequency AC ramp, such as 10%, 20%, 30%, 40%, 50%, 60%, 70%, 80%, 90%, 100%, 120%, 140%, 160%, 180%, 200% or greater than the peak of the high frequency AC ramp. Where the shock is monophasic, the shock duration may be 4-16 ms. Where the shock is biphasic, the first phase may be 2-6 ms and the second phase may be 2-12 ms. The shock is preferably applied at the peak or end of the HFAC ramp.

As will be appreciated by one skilled in the art, in various aspects and embodiments of the invention, the device may be configured to apply alternating current manually at the discretion of a health care worker, either by an internally implanted or externally applied device, or may be applied automatically in response to a detected arrhythmia, either by an implanted or externally disposed device. Such applications may coincide with detection of arrhythmia in the subject by a sensing circuit allowing detection of the arrhythmia, which may be included in or external to the device.

The device and methodology may be used to treat a number of different types of arrhythmias. Typically, the arrhythmia is a tachyarrhythmia, such as ventricular tachyarrhythmia, or atrial tachyarrhythmia. Ventricular tachyarrhythmias may include, but are not limited to ventricular fibrillation. Atrial tachyarrhythmias may include, but are not limited to atrial fibrillation and atrial flutter.

The device and methodology utilize a plurality of electrodes which may be configured in a variety of ways to administer alternating current. Alternating current may be administered via a number of electrode configurations as described. When used with an externally applied device, the alternating current is preferably applied via large electrodes placed on the skin across the heart as is typically done with external defibrillators. Automatic response to arrhythmia detection can be implemented using separate skin electrodes to detect the ECG, or using the same large electrodes through which the alternating current is then applied.

When used with an implanted device, the alternating current is preferentially applied via electrodes placed in or about the cardiac chambers, or via electrodes placed in the chest outside the rib cage, for example in the subcutaneous layers including the housing of the implanted device itself, or using a combination of such electrodes. Automatic response to arrhythmia detection can be accomplished using electrodes placed in or about the cardiac chamber or chambers susceptible to tachyarrhythmia, or using electrodes placed in the chest outside the ribcage, for example in the subcutaneous layers.

In one configuration, a device may be in electrical communication with a subject's heart by way of one or more leads, suitable for delivering multi-chamber stimulation and pacing therapy. Not every configuration has all of the electrodes to be described below, but a particular configuration may include some of these electrodes. Other configurations of the device may include even more electrodes than discussed herein. For example, alternating current may be applied by other, additional electrodes than those described below. Further, the electrodes and device may be configured to apply alternating current using a tiered approach. Additional electrodes for delivering alternating current can include combinations or electrodes situated over the epicardium (e.g., multiple pacing and relatively larger surface area defibrillation electrodes that may be used for optimizing cardiac resynchronization therapy and providing defibrillation).

Regarding the leads and electrodes, in order to sense atrial cardiac signals and to provide right atrial chamber stimulation therapy, the device may be coupled to an implantable right atrial lead, typically having an atrial tip electrode and an atrial ring electrode, which may be implanted in the subject's right atrial appendage. The device is also known as and referred to as a pacing device, a pacing apparatus, a cardiac rhythm management device, or an implantable cardiac stimulation device.

To sense left atrial and ventricular cardiac signals and to provide left atrial and ventricular pacing therapy, the device may be coupled to a "coronary sinus" lead configured for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, a coronary sinus lead may be configured to receive atrial and ventricular cardiac signals and to deliver left ventricular pacing therapy using a left ventricular (LV) tip electrode and a LV ring electrode. Left atrial pacing therapy may use, for example, first and second left atrial (LA) ring electrodes. Administration of alternating current can also be performed using at least a coronary sinus coil electrode. Administration of alternating current can also be performed using a pair of right atrial (RA) ring electrodes.

The device may also be in electrical communication with a subject's heart by way of an implantable right ventricular lead, typically having a right ventricular (RV) tip electrode, an RV ring electrode, an RV coil electrode, and a superior vena cava (SVC) coil electrode (also known as a right atrial (RA) coil electrode).

The components of the device may be contained in a case, which is often referred to as the "can", "housing", "encasing", or "case electrode", and may be programmably selected to act as the return electrode for unipolar operational modes. The case may further be used as a return electrode alone or in combination with one or more additional electrodes for stimulating purposes. The case may further include a connector having a plurality of terminals for connecting one or more of the following electrodes in various configurations:

a left ventricular tip electrode;
a left ventricular ring electrode;
a left atrial coil electrode;
a left atrial ring electrode(s);
a coronary sinus coil electrode;
a right ventricular tip electrode;
a right ventricular ring electrode;
a right ventricular RV coil electrode;
right atrial ring electrode(s);
a right atrial tip electrode;
a right atrial SVC coil electrode;
an epicardial electrode; and
subcutaneous electrode(s).

The device and methodology described herein includes tiered therapy, which provides an adaptive and refined therapy for arrhythmias. The tiered approach divides therapy for arrhythmias into a progression of multiple tiers. For example, tiered therapy may include applying alternating current along a progression of different frequencies and durations, the progression continuing until the arrhythmia is terminated.

The progression of tiered therapy may proceed from a least invasive frequency and duration (e.g., vector) to a more invasive vector, stopping the progression whenever the arrhythmia ceases. In some implementations, the progression of vectors reflects a progression in the size of electrodes used to deliver alternating current, and/or a progression in the area or volume of electrically excitable cardiac tissue to be stimulated. This exemplary technique of tiering the vectors may minimize pain, especially if the patient is responsive to the least invasive vector.

As will be appreciated by one skilled in the art, various aspects of the methodology of the present invention may be combined. For example, tiered therapy may also include application of electric shock in addition to application of AC. For example monophasic or biphasic shock may be administered after or before AC is applied in a tiered approach.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Reversible Conduction Block in Cardiac Tissue Using Sinusoidal Alternating Current Field Stimulation The following experimental methods were followed in this example.

Cell culture was performed as follows. Neonatal rat ventricular myocytes (NRVMs) were dissociated from 2-day old Sprague-Dawley rat hearts with the use of the enzymes, trypsin and collagenase, as previously described (see, Iravanian et al., *AJP Heart Circ.*, 285(1):H4449-56 (2003)). The resulting cell suspension was plated at high density onto 21 mm diameter plastic coverslips (106 myocytes per coverslip) to form monolayers that became confluent after 3-4 days of culture. Experiments were performed on days 6 to 8 after plating. For reentry experiments, prior to plating, a 4-mm diameter hole was punched in the coverslip.

Electrophysiological recording was performed as follows. Transmembrane voltage was recorded using contact fluorescent imaging as previously described (see, Entcheva et al., *J Cardiovasc Electrophysiol.*, 11(6):665-76 (2000)). Briefly, maps of transmembrane potential were recorded by placing the cell monolayer directly on top of a bundle of 253 optical fibers 1 mm in diameter, arranged in a tightly packed, 17-mm-diameter hexagonal array. The cell monolayers were stained during the experiment with 10 µM di-4-ANEPPS, a fluorescent voltage-sensitive dye, and continually superfused with warmed (37° C.) Tyrode's solution (in mmol/L: 135 NaCl, 5.4 KCl, 1.8 CaCl2, 1 MgCl2, 0.33 NaH2PO4, 5 HEPES, 5 glucose).

Electric field stimulation was applied across a parallel set of platinum wires 2.5-cm long placed in the bath outside the monolayer preparation. The field intensity was calibrated from the peak voltage across a pair of AgCl test electrodes placed at a 1.4-cm spacing in the chamber.

The following experimental protocol was used to perform conduction experiments. A bipolar point electrode was placed near the edge of the monolayer and used to pace the monolayer at 2-6 Hz (10 ms monophasic pulse, 1.5× threshold). Each recording was 3 sec long, with point pacing either on for the entire recording or turned off for the last 500 ms. After 1 sec, a 1-sec duration AC or DC pulse was applied to the monolayer. For reentry experiments, rapid point pacing was used to induce a stable spiral wave reentry. Stable reentry was considered successful if the wave pinned to the hole for at least 1 min. Each recording was 3 sec, in which a 1-sec duration AC or DC pulse was applied to the monolayer 1 sec after the start of the recording.

Signal processing was performed as follows. Over the duration of the optical recording, the voltage fluorescence baseline decreased due to photobleaching and heating of the LED excitation light source. Baseline drift was corrected for by subtraction of a fitted third-order polynomial at each recording site. The individual signals were also temporally filtered using a 5-point median filter and range normalized from 0 to 1. Voltage maps were created by interpolating the mapped data to a 100 μm×100 μm grid. Recording channels with poor signal were not used for the interpolation.

Data analysis was performed as follows. For conduction experiments, monolayer responses to DC and AC field were categorized as no effect, field-evoked activity (FEA), or conduction block during the field pulse. In no effect cases, pace conduction continued at the same pacing rate during the field pulse. In FEA cases, rapid activity faster than the point pacing rate was elicited. In conduction block cases, no activation occurred during the field pulse. The occurrence of post-pulse ectopic activity (PPEA) was separately identified, when multiple spontaneous waves were initiated at a location distinct from the point pacing site.

For reentry experiments, monolayer responses were characterized as no effect, FEA+termination, termination, or reinitiation. In no effect cases, the field did not perturb the spiral wave reentry. In FEA+termination cases, FEA was present during the pulse and ceased at field offset. In termination cases, the reentry terminated at field onset, and no activity was present during the pulse. In reinitiation cases, activity during or after the pulse reinitiated a spiral wave.

The following computational methods were followed.

A cell monolayer model was set-up and represented by a 4.4 cm×4.4 cm×0.25 mm tissue mesh centered at the bottom of a perfusate-filled chamber. The electrical properties of the tissue were modeled using an isotropic bidomain representation. To mimic the random orientation of the myocytes in the monolayer, the intracellular conductivities were varied randomly (Plank et al., *J Cardiovasc Electrophysiol*, 16(2): 205-216 (2005)). Membrane kinetics of the monolayer were represented using the Luo-Rudy dynamic guinea pig veuirieular model (Faber et al., *Diophys J*, 78(5):2392-2404 (2000)), with modifications for modeling large external field stimulation (Ashihara et al., *Europace*, 7(s2), S155-S165)).

A simulation protocol was also used. In conduction block simulations, a point electrode was used to pace the tissue at 2 Hz before, during, and after the AC field pulse. In reentry simulations, an 8-mm hole was introduced in the center of the monolayer to allow attachment of the spiral wave. A spiral wave was initiated using an S1-S2 cross-stimulation protocol. A one second-duration AC field pulse was then applied at varying field strengths and frequencies. AC field stimulation was delivered from line electrodes located in the superfusing bath, as in the experimental setup.

The following results were observed.

AC Electric Field Stimulation During Pacing: The effect of 1 second AC electric field stimulation on propagation of paced impulses across confluent monolayers (n=15) of neonatal rat ventricular cardiomyocytes was explored. At the highest field strength tested in our study (22 V/cm), AC field frequencies between 50 Hz and 1 kHz consistently resulted in a conduction block across the monolayer (FIGS. 3A and 5A). During the AC field stimulus, the cells were held at an elevated transmembrane voltage and point pacing-initiated conduction was completely blocked. Immediately following cessation of the AC field, the transmembrane voltage ($V_m$) returned back to the initial resting potential, and subsequent paced stimuli initiated propagating waves across the monolayer with conduction velocity and propagation pattern unchanged from those before AC field stimulation. The results were consistent across all the monolayers tested.

The degree of conduction block was frequency- and field strength-dependent. At the highest field strength tested (22 V/cm), AC frequencies less than 50 Hz resulted in repetitive depolarizations of the monolayer, which we term field-evoked activity (FEA) (FIGS. 3B and 5A), while frequencies above 2 kHz had no effect on the monolayer (FIGS. 3C and 5A). FEA was also elicited at lower field strengths (<10 V/cm) for all frequencies below 2 kHz (FIG. 5A).

Figure 4:
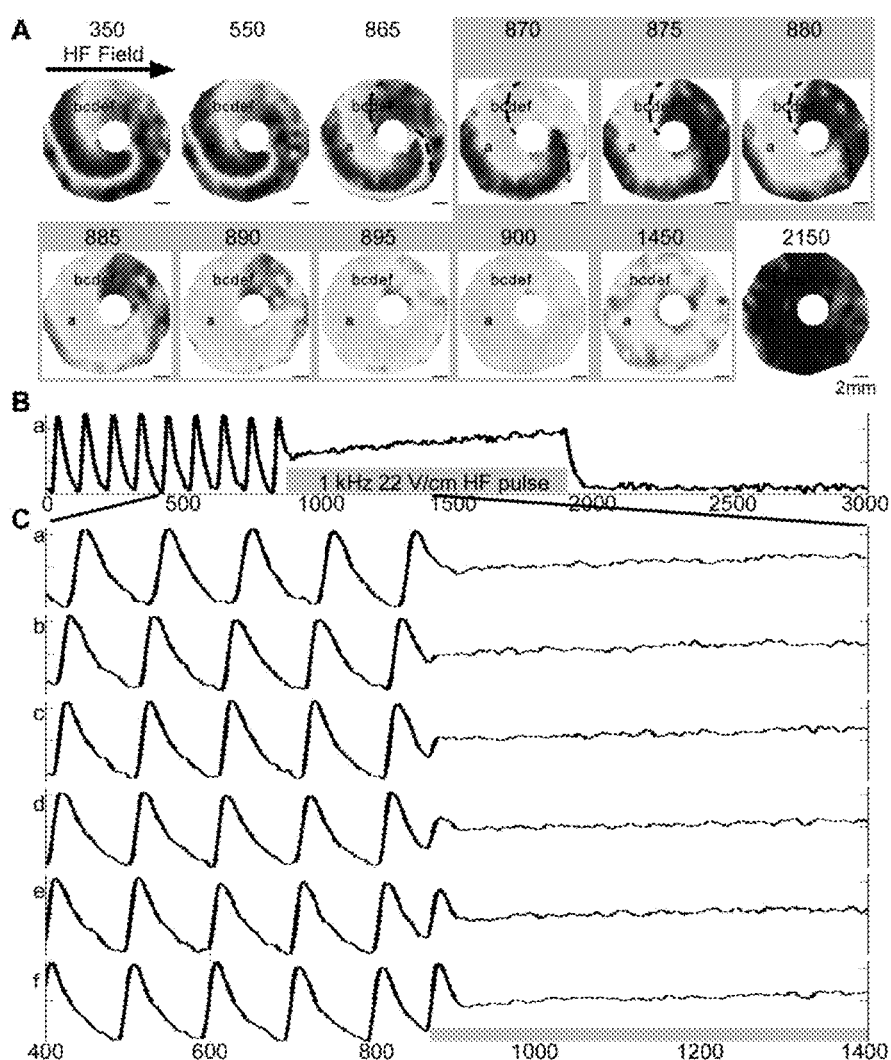
FIGS. 4A, 4B and 4C show graphical representations of AC electric field pulse terminating pinned spiral wave reentry.
Figure 5:
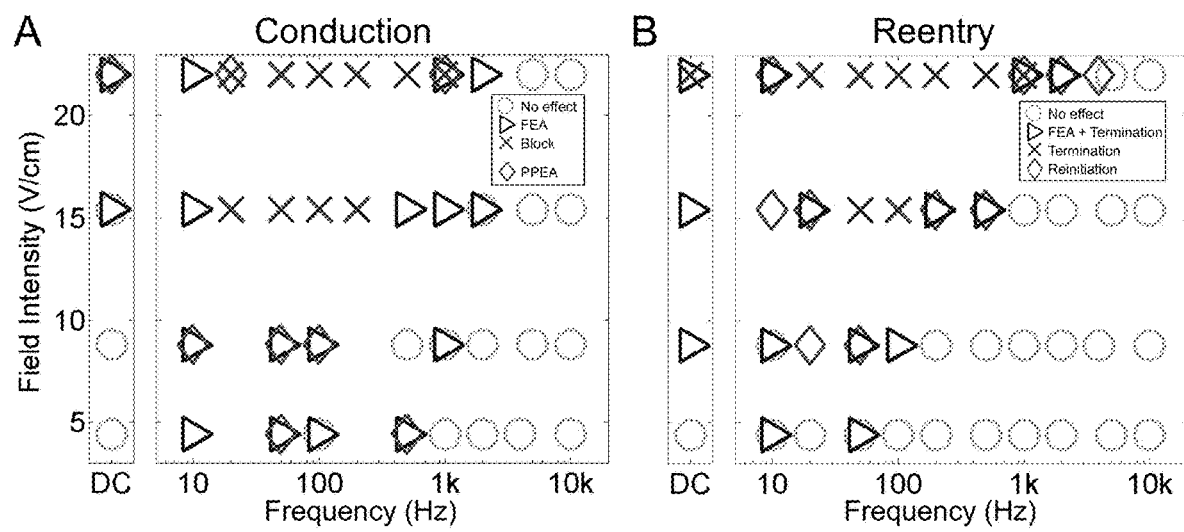
FIGS. 5A and 5B show graphical representations summarizing data of DC and AC field pulse effects on conduction (n=15 monolayers) and reentry (n=11). Not all field strengths and frequencies were tested in each monolayer.

Termination of Spiral Wave Reentry by Sustained AC field: Next, the ability of sustained AC-induced conduction block to terminate stable spiral wave reentry in monolayers (n=11) was evaluated. AC fields of 22 V/cm with frequencies between 20 Hz and 1 kHz consistently terminated spiral wave reentry. The onset of the AC field depolarized the entire excitable gap and held $V_m$ at an elevated level for the field duration, completely extinguishing the spiral wave and preventing re-initiation of activity (FIGS. 4 and 5B). Following AC field cessation, $V_m$ returned to the resting potential, followed by quiescence. Subsequent pacing stimuli were able to elicit normal propagated waves (not shown).

AC frequencies <50 Hz or >2 kHz often resulted in FEA during the AC field pulse followed by either termination of spiral wave reentry or re-initiation of new spiral wave reentry at the offset of the pulse (FIG. 5B). AC fields at even higher frequencies (5-10 kHz) had no appreciable effect on spiral wave reentry. As with conduction block, the field strength threshold for spiral wave termination was frequency-dependent (FIG. 5B).

AC Field vs. Direct Current Field: Point-pacing during the DC field initiated new propagating waves, indicating lack of conduction block (FIG. 5A). A second rapid depolarization was observed at the field offset. Following cessation of the DC field, in all cases, the monolayer was severely damaged, identified by a rapid decline in optical signal intensity and point pacing initiating highly heterogeneous propagation, producing rapid ectopic activity, or failing to elicit any response. High-strength DC field stimulation terminated spiral wave reentry by depolarization of the entire excitable gap, similarly to that observed during AC field stimulation (FIG. 5B). However, as during conduction experiments, during the DC field pulse $V_m$ returned near the resting potential, FEA was frequently initiated, and the monolayer was severely damaged. Lower-strength (≤15 V/cm) DC field pulses either initiated FEA or elicited no effect at the lowest field strengths tested (FIGS. 5A and B).

Computational Modeling of Reentry Termination and Conduction Block by AC: Computer simulations were used of a three-dimensional bidomain model of guinea pig ventricular tissue to dissect the biophysical mechanisms of conduction block by sustained AC field stimulation.

Figure 6:
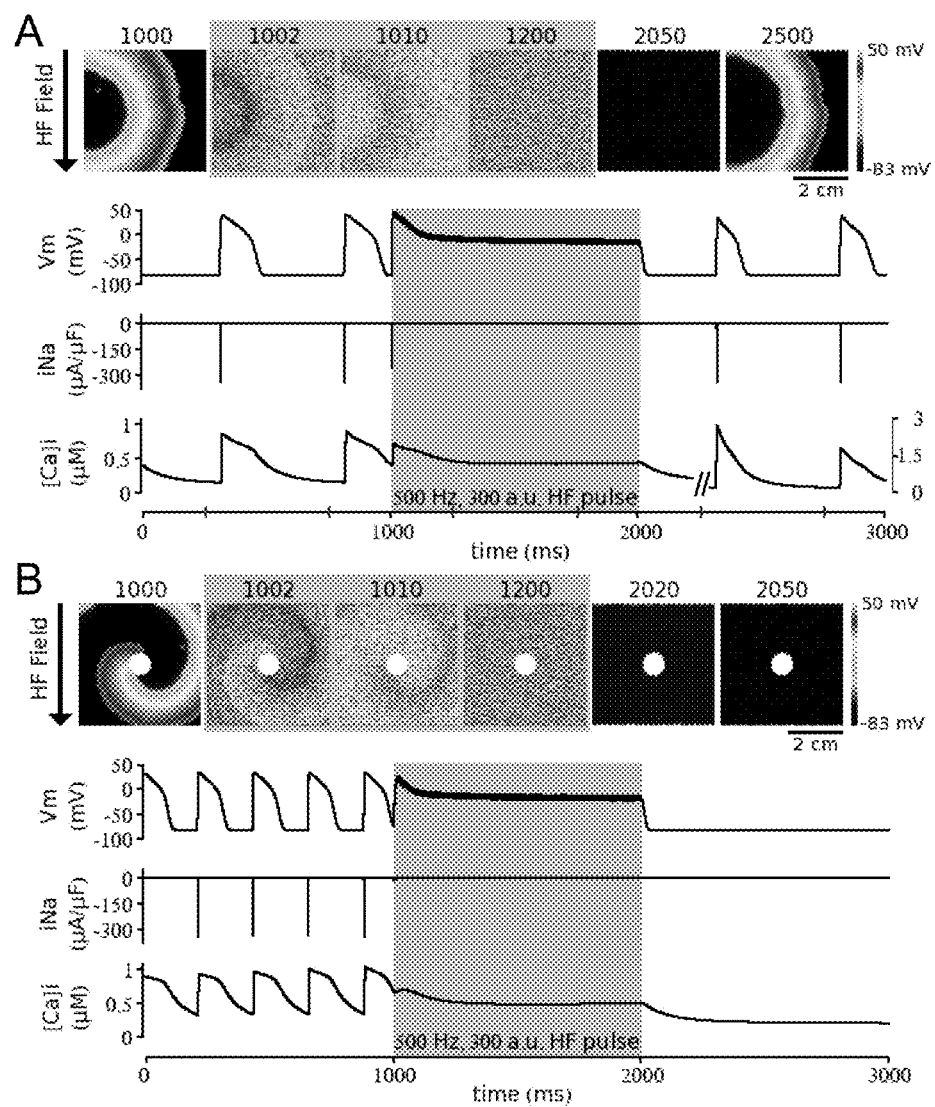

Consistent with our monolayer experiments, simulations revealed conduction block of paced waves and termination a stable spiral wave reentry (FIG. 6) during sustained AC field stimulation. Both conduction and reentry simulations revealed that $V_m$, oscillates around an elevated average value ranging from −10 to −20 mV during the AC field pulse. The functional consequence of the sustained AC field is a "paralytic" effect that prevents sodium channel recovery from inactivation after $V_m$ exceeds the sodium channel activation threshold (−58.8 mV). Intracellular calcium is maintained at an elevated level during the pulse, returning to resting levels at field offset (FIG. 6).

The findings discussed herein reveal an important biophysical effect of sustained AC on cardiac tissue that is distinctly different from DC field stimulation. DC field causes a make excitation at its onset and a break excitation at its offset, and $V_m$ returns to resting potential in between, provided sufficient time between field onset and offset. On application of AC, $V_m$ is elevated and oscillates around an elevated value ranging from −10 to −20 mV, blocking conduction and preventing re-initiation of activity.

Computational modeling provided insight into the ionic mechanism of conduction block. $V_m$ oscillated in phase with the frequency of AC field, but average $V_m$, during the field application was elevated above the sodium channel activation threshold, indicating that the conduction block is due in part to the sustained inactivation of cardiac sodium channels. The simulation parameter space of the guinea pig model closely matched the experimental parameter space of neonatal rat cells, demonstrating that these mechanisms are not species-dependent.

EXAMPLE 2

AC Applied to Whole Hearts

This example presents data showing termination of fibrillation in whole guinea pig hearts in vivo upon application of AC.

Guinea pigs were perfused as Langendorff. preparations. Hearts were stained with the voltage-sensitive dye di-4-ANEPPS (10 µmol/L) by direct coronary perfusion for 10 minutes. An EC uncoupler (diacetyl monoxime) was used to arrest mechanical deformation and the hearts were placed in a custom-built chamber that was attached to a micromanipulator. Optical action potential mapping was performed from 128 sites of the intact guinea pig heart. Total mapping field was 1 cm×1 cm with an estimated depth of field of 0.2 mm. The ventricular epicardial surface was stimulated using bipolar electrodes to induce ventricular fibrillation. Two field electrodes placed on either side of the heart delivered the AC electric field.

Figure 7:
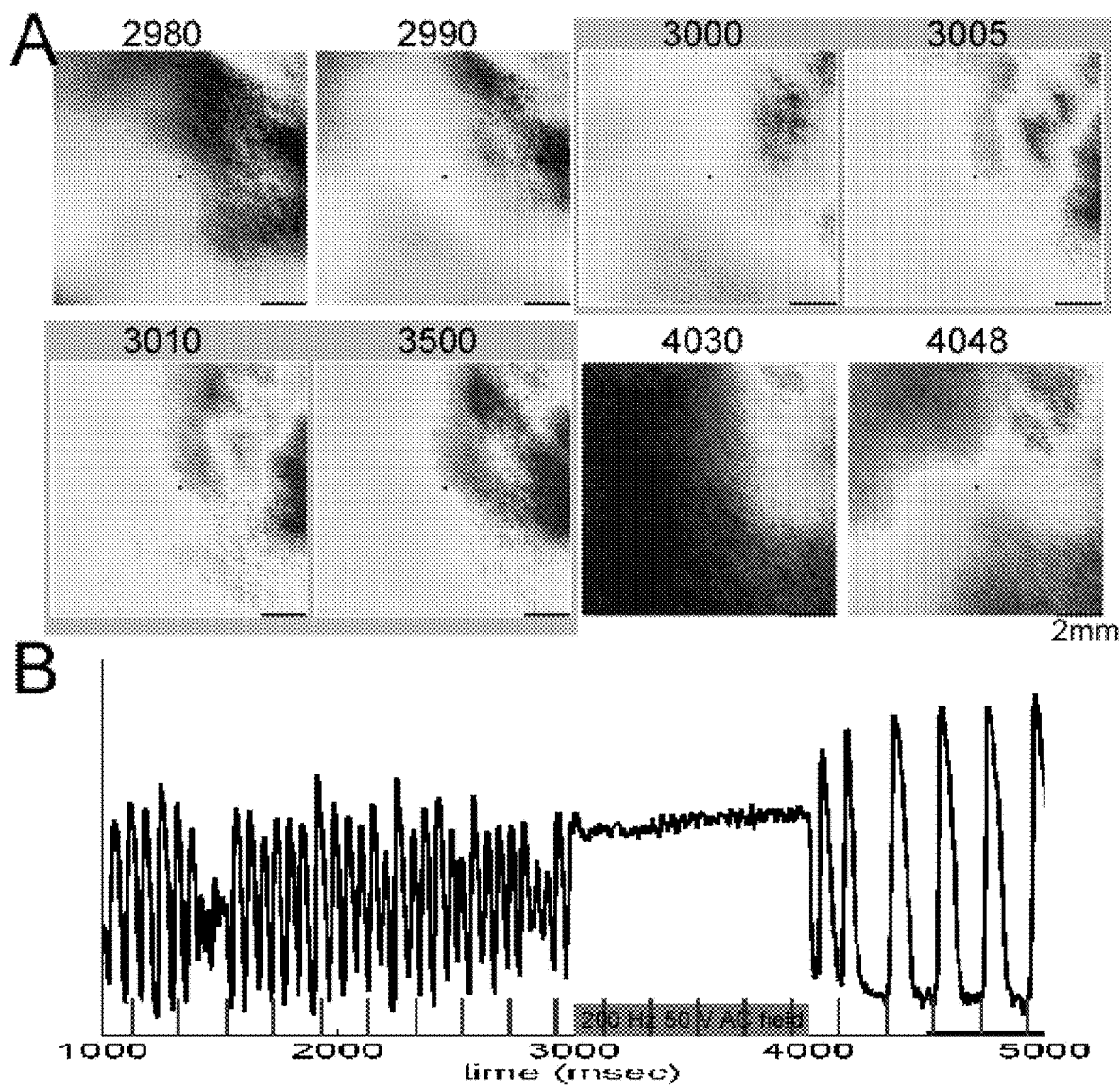
FIG. 7 shows graphical representations of defibrillation of a whole heart by a 1 second duration pulse of AC.
Figure 8:
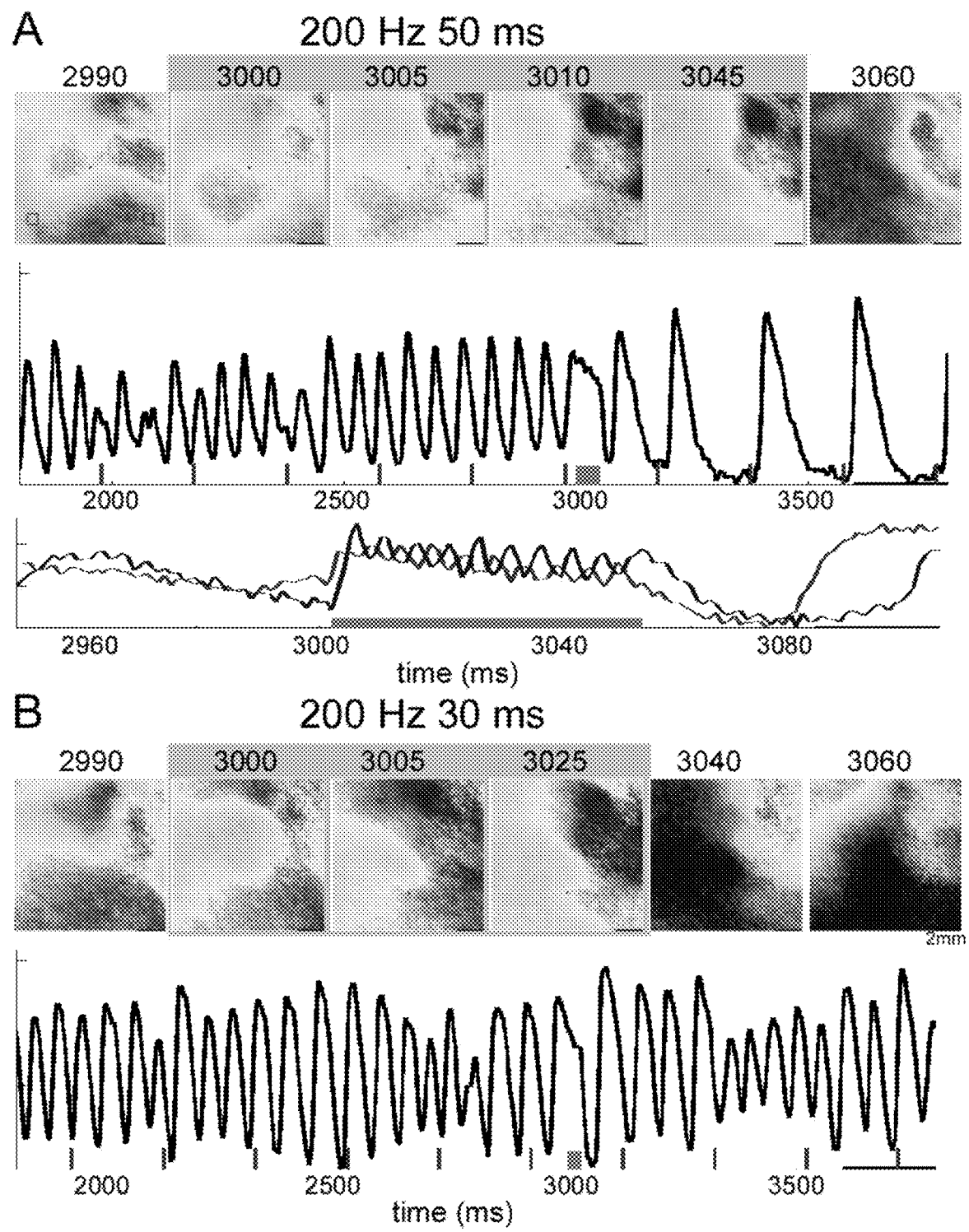
FIG. 8 shows graphical representations of successful defibrillation of a whole heart by a 50 ms pulse (A) and failed defibrillation by a 30 ms pulse (B).

Pulses of AC administered to whole guinea pig hearts was performed. As shown in FIG. 7, defibrillation of a whole heart is evidenced by a 1 second pulse of AC. As shown in FIG. 8, successful defibrillation of a whole heart by a 50 ms pulse (A) and failed defibrillation by a 30 ms pulse (B) is evidenced at a frequency of 200 Hz.

EXAMPLE 3

Administration of Ramped Waveform

This example presents data showing administration of high frequency AC having a ramped waveform to skeletal muscle of adult swine.

Figure 9:
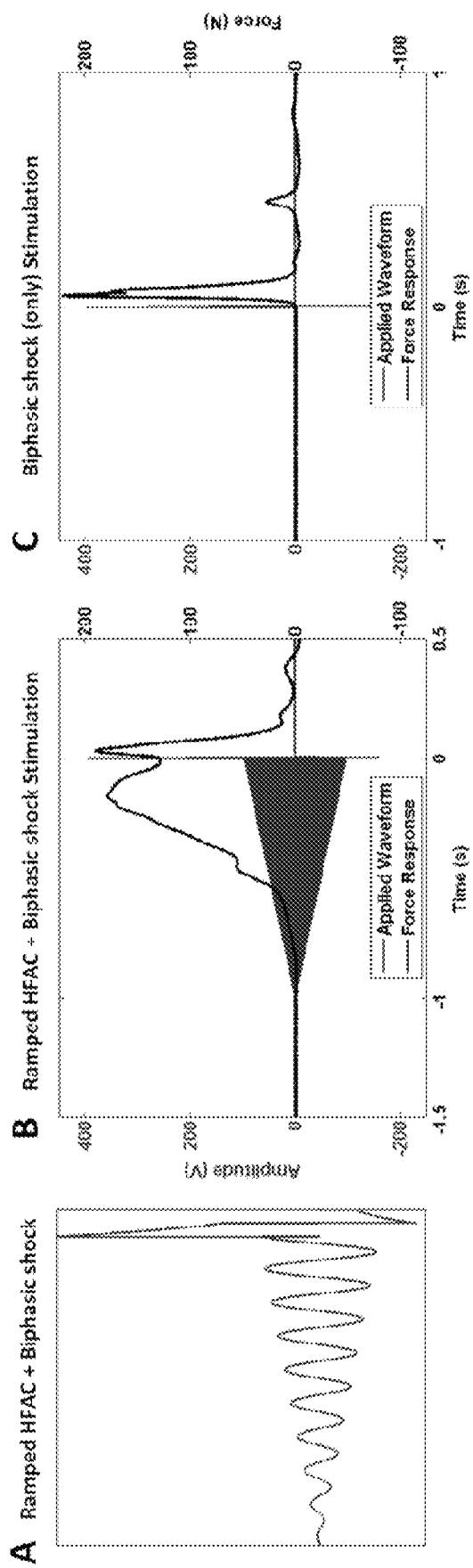
FIGS. 9A, 9B and 9C show graphical representations of administration of a ramped high frequency AC waveform plus biphasic shock and subsequent response thereto.

In experiments in adult swine, an accepted surrogate of shock-induced pain, the effect of high frequency AC on skeletal muscle stimulation was tested and compared with that observed during standard ICD shocks as control. Application of high frequency AC (1 kHz) ramped in amplitude from 0 to 100 V over 1 sec (FIG. 9A) to the hind limb produced a gradual tetanic muscle contraction without significant further muscle response to 400 V biphasic shock immediately following the high frequency AC ramp (FIG. 9B), whereas application of a 400 V standard biphasic shock alone elicited a sudden sharp contraction of the limb (FIG. 9C), like that seen during cardiac defibrillation. HFAC blunts the amplitude and especially the rate of force developed in skeletal muscle, which results in substantial mitigation of defibrillation-induced pain.

Although the invention has been described with reference to the above examples, it will be understood that modifications and variations are encompassed within the spirit and scope of the invention. Accordingly, the invention is limited only by the following claims.

What is claimed is:

1. A device comprising:
    a plurality of electrodes configured to be applied to a patient, wherein the electrodes are configured for external positioning on the patient;
    a housing configured to be positioned external to the patient and
    a waveform generator configured to generate an alternating current (AC) and an electrical shock which are applied to the electrodes, the waveform generator being disposed in the housing;
    wherein the electrical shock is at least 400 volts (V), and wherein the AC has a frequency in a range between 50 Hz to 20 kHz, has a duration, and includes a ramped amplitude waveform defined by a gradually increasing peak-to-peak amplitude of the AC during at least sixty percent of the duration.

2. The device of claim 1, wherein the AC has a frequency between about 50 Hz to 300 Hz.

3. The device of claim 1, wherein the device is configured to administer the AC after a delay from onset of cardiac excitation.

4. The device of claim 1, wherein the electrical shock is a biphasic electrical shock following application of the AC.

5. The device of claim 1, wherein the AC has a frequency between 50 Hz and 500 Hz.

6. The device of claim 1, wherein the AC has a frequency between 500 Hz and 1 kHz.

7. The device of claim 1, wherein the AC has a frequency between 250 Hz and 500 Hz.

8. The device of claim 1, wherein the electrical shock is applied by the waveform generator immediately after the end of the AC.

9. The device of claim 1, wherein the peak-to-peak amplitude of the AC increases until the application of the electrical shock.

10. The device of claim 1, wherein the peak-to-peak amplitude of the AC increases throughout the duration of the AC.

11. The device of claim 1, wherein the ramped amplitude waveform is a gradually increasing sine wave.

12. The device of claim 1, wherein the ramped amplitude waveform is a gradually increasing triangular wave.

13. The device of claim 1, wherein the ramped amplitude waveform is a gradually increasing square wave.

14. The device of claim 1, wherein the electrical shock is administered after offset of the AC.

15. The device of claim 1, wherein the electrical shock is administered after onset of the AC and no later than offset of the AC.

16. The device of claim 1, wherein the duration in a range of 0.25 to 5 seconds.

17. The device of claim 1, wherein the duration in a range of 0.1 to 2.0 seconds.

18. The device of claim 1, wherein the gradually increasing peak-to-peak amplitude increases for at least seventy percent of a duration of the AC.

19. The device of claim 1, wherein the electrical shock is a biphasic electrical shock following application of the AC.

20. A device for treating arrhythmia comprising:
at least one electrode configured to be applied externally to a torso of a patient;
a waveform generator configured to generate an alternating current (AC) and an electrical shock which are applied to the at least one electrode; and
a computer, logic circuit, or microprocessor configured to command the waveform generator to generate or deliver alternating current (AC) and the electrical shock to the at least one electrode;
wherein the waveform generator is configured to generate the alternating current (AC) to have a frequency between 50 Hz and 20 kHz and a duration;
wherein during at least sixty percent of the duration, the AC is defined by a ramped amplitude waveform having a gradually increasing peak-to-peak amplitude of the AC, and
wherein the electrical shock is at least 400 volts (V).

21. The device of claim 20, wherein the waveform generator is configured to generate an alternating current (AC) having a frequency between 50 Hz and 500 Hz.

22. The device of claim 20, wherein the waveform generator is configured to generate an alternating current (AC) having a frequency between 500 Hz and 1 kHz.

23. The device of claim 20, wherein the waveform generator is configured to generate an alternating current (AC) having a frequency between 250 Hz and 500 Hz.

24. The device of claim 20, wherein the device is configured to generate and administer a biphasic electrical shock following application of AC.

25. The device of claim 20, wherein the device is configured to generate and administer a biphasic electrical shock following application of AC.

26. The device of claim 20, wherein the electrical shock is administered after offset of the AC, or after onset of the AC and before offset of the AC.

27. The device of claim 20, wherein the duration is in a range of 0.025 to 5 seconds.

28. The device of claim 20, wherein the duration is at least 0.050 seconds and the ramped waveform rises for at least seventy percent of the duration.

29. The device of claim 20, wherein the duration is at least 0.100 seconds and the ramped waveform rises for at least eighty percent of the duration.

30. A device for treating arrhythmia comprising:
a plurality of electrodes configured to be applied to a patient;
a housing configured to be positioned internal or external to the patient and a waveform generator configured to generate an alternating current (AC) and an electrical shock which is applied to the electrodes, the waveform generator being disposed in the housing;
wherein the electrical shock is at least 400 volts (V), and
wherein the AC has a frequency in a range between 50 Hz to 20 kHz, has a duration, and includes a ramped amplitude waveform defined by a gradually increasing peak-to-peak amplitude of the AC during at least sixty percent of the duration.

31. The device of claim 30, wherein the waveform generator is configured to generate AC having a frequency between about 50 Hz to 300 Hz.

32. The device of claim 30, wherein the electrodes are configured for intravascular or intracardiac positioning in the patient.

33. The device of claim 30, wherein the electrodes are configured for extravascular or external positioning on the patient.

34. The device of claim 30, wherein the device further comprises a sensing circuit for determining the presence of arrhythmia.

35. The device of claim 34, wherein the device automatically generates the AC when arrhythmia is detected.

36. The device of claim 30, wherein the device is implantable.

37. The device of claim 34, wherein the device further comprises a programmable logic circuit, such that the device is configured to administer AC after a delay from onset of cardiac excitation.

38. The device of claim 30, wherein the electrical shock is a biphasic electrical shock following application of AC.

39. The device of claim 30, wherein the waveform generator is configured to produce an alternating current (AC) having a frequency between 50 Hz and 500 Hz.

40. The device of claim 30, wherein the waveform generator is configured to produce alternating current (AC) having a frequency between 500 Hz and 1 kHz.

41. The device of claim 30, wherein the waveform generator is configured to produce an alternating current (AC) having a frequency between 250 Hz and 500 Hz.

* * * * *